United States Patent
Blair et al.

(10) Patent No.: US 7,837,648 B2
(45) Date of Patent: Nov. 23, 2010

(54) MEDICAMENT DISPENSING SYSTEM

(75) Inventors: Edward Duncan Blair, Stevenage (GB); Liqun Yang, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1711 days.

(21) Appl. No.: 10/496,440

(22) PCT Filed: Nov. 21, 2002

(86) PCT No.: PCT/EP02/13151

§ 371 (c)(1), (2), (4) Date: Oct. 20, 2004

(87) PCT Pub. No.: WO03/043684

PCT Pub. Date: May 30, 2003

(65) Prior Publication Data

US 2005/0043674 A1    Feb. 24, 2005

(30) Foreign Application Priority Data

Nov. 22, 2001    (GB)    ................... 0127989.2

(51) Int. Cl.
- A61M 31/00    (2006.01)
- A61M 11/00    (2006.01)
- A61B 5/08    (2006.01)

(52) U.S. Cl. ...................... 604/67; 600/532; 128/200.14

(58) Field of Classification Search ............... 604/890.1, 604/891.1, 65–67, 503, 504; 128/200.14, 128/200.19; 73/23.3; 600/347, 532, 529
See application file for complete search history.

(56) References Cited

U.S. PATENT DOCUMENTS

| | | | |
|---|---|---|---|
| 5,002,055 A | 3/1991 | Merki et al. | |
| 5,772,085 A | 6/1998 | Bryant et al. | |
| 5,860,419 A | 1/1999 | Davies et al. | |
| 5,954,050 A | 9/1999 | Christopher | |
| 6,269,810 B1 * | 8/2001 | Brooker et al. | 128/203.12 |
| 6,609,068 B2 * | 8/2003 | Cranley et al. | 702/24 |
| 2008/0221557 A1 * | 9/2008 | Santini et al. | 604/891.1 |

FOREIGN PATENT DOCUMENTS

| | | |
|---|---|---|
| DE | 19545130 | 6/1997 |
| EP | 0372777 | 6/1990 |
| EP | 0689848 | 1/1996 |
| WO | WO 95/22365 | 8/1995 |

(Continued)

OTHER PUBLICATIONS

Ziegler et al., "Biosensor development," *Current Opinion in Chemical Biology* 2(5):585-591 (1998).

*Primary Examiner*—Kevin C Sirmons
*Assistant Examiner*—Catherine N Witczak
(74) *Attorney, Agent, or Firm*—James P. Riek (57) ABSTRACT

A medicament dispensing system for treatment of a disease is disclosed, the system comprising: (i) detecting means for detecting one or more biochemical marker(s) indicative of the disease; (ii) electronic processing means for processing information obtainable from the detecting means; and (iii) medicament dispensing means for dispensing a quantity of medicament determinable by the electronic processing means. The medicament dispensing system is particularly useful for the treatment of respiratory disorders, such as asthma, or for other disorders which may be treated by inhalation, either through the nose or mouth.

28 Claims, 3 Drawing Sheets

FOREIGN PATENT DOCUMENTS

| WO | WO 99/06825 | 2/1999 |
| WO | 9944664 A2 | 9/1999 |
| WO | 00/53247 | 9/2000 |
| WO | WO 01/24690 | 4/2001 |
| WO | WO 01/26020 | 4/2001 |
| WO | WO 01/26021 | 4/2001 |

* cited by examiner

MEDICAMENT DISPENSING SYSTEM

This application is filed pursuant to 35 USC 371 as a United States National Phase Application of International Patent Application Ser. No. PCT/EP02/13151 filed on 21 Nov. 2002, which claims priority from GB 0127989.2 filed on 22 Nov. 2001 in the United Kingdom.

The present invention relates to a novel medicament dispensing system for treatment of a disease, the system being able to provide diagnostic information relating to the extent and severity of the disease and being arranged to dispense an appropriate quantity of medicament, wherein the medicament is the adjustable dosage of one or more drugs in a fixed or variable combination.

BACKGROUND TO THE INVENTION

Many people who suffer from a chronic disease require regular medication to ensure adequate control of the disease. For example, asthmatics normally require a daily dose of an anti-inflammatory drug to prevent an asthma attack. In addition, asthmatics often require a different dose and/or a different anti-inflammatory drug to treat an asthma attack. In each case, the amount of drug required by the patient will depend on the severity of the asthmatic condition or the severity of asthma attack. At present, a patient is supplied with an inhaler device which dispenses a pre-determined quantity of medication, and which does not take into account the precise present day condition of the patient. WO95/22365 discloses an inhaler that measures a specific feature of the disease, for example the inhalation airflow, and processes this information to advise the patient, inter alia, on changes in timings or dosages of drug to be taken. It is however, up to the patient to implement these changes. Furthermore, any changes in drug dosage will be based on the patient's condition at the time the previous dose was administered and not the current condition of the patient.

BRIEF SUMMARY OF THE INVENTION

It is therefore an object of the present invention to provide an integrated medicament dispensing system that is able determine the dosage of medicament required and dispense this dosage, so that the patient is receiving the appropriate dosage for his condition at that time.

Accordingly, the invention provides a medicament dispensing system for treatment of a disease, the system comprising:
(i) detecting means for detecting one or more biochemical marker(s) indicative of said disease;
(ii) electronic processing means for processing information obtainable from the detecting means; and
(iii) medicament dispensing means for dispensing a quantity of medicament determinable by the electronic processing means.

In one aspect of the invention, the detecting means, electronic processing means and medicament dispensing means are integrated in a single device. The device is suitably configured as a portable or handheld device.

In another aspect, the detecting means is provided as an attachment to the medicament dispensing means. Suitably, communication (e.g. via a docking interaction) exists between the detecting means and the medicament dispensing means.

In a further aspect, the detecting means is remote to the medicament dispensing means. Suitably, communication (e.g. via wireless means) exists between the detecting means and the medicament dispensing means.

In a still further aspect, the detecting means and medicament dispensing means are integrated in a single device and the electronic processing means exists as a standalone unit.

DETAILED DESCRIPTION OF THE INVENTION

The medicament dispensing system herein comprises detecting means for detecting one or more biochemical marker(s) indicative of a disease state.

Certain biochemical markers are indicative of a given disease and can be used to determine the current extent and severity of the disease. Examples of such biochemical markers include, but are not limited to: eicosanoids, such as prostanoids (e.g. $PGE_2$, $PGF_{2\alpha}$, $TxB_2$), leukotrienes (e.g. LTB4, $LTC_4$, $LTD_4$, $LTE_4$, $LTF_4$), isoprostanes (e.g. $F_2$-isoprostanes, 8-epi-$PGF_2$ (8-isoprostane)); nitric oxide related products, such as nitric oxide (NO), nitrotyrosine, nitrite ($NO_2^-$), nitrate ($NO_3^-$), s-nitrosothiols (SNO); hydrogen peroxide ($H_2O_2$); lipid peroxidation products, such as thiobarbituric acid-reactive substances, phospholipidester, cholesterylester, hydroperoxides, aldehydic lipid peroxidation products (e.g. 4-hydroxynonenal, fluorescent protein adducts (e.g. lipofuscin), conjugated dienes and antioxidants; vasoactive amines, such as acetylcholine, serotinin, histamine, catecholamines, cortisol and thyroxine; electrolytes, such as $Na^+$, $Cl^-$, $Mg^{2+}$, $Ca^{2+}$; ammonia; hydrogen ions; proteins; cytokines, such as interleukin-$1_\beta$ (IL-$1_\beta$), interleukin-2 (IL-2), interleukin-6 (IL-6), tumour necrosis factor $\alpha$ (TNF-$\alpha$) and interleukin-8 (IL-8); carbon monoxide (CO); and exhaled hydrocarbons, such as ethane, propane, butane, pentane, isoprene. Detection and quantification of these biochemical markers will enable the extent and severity of the disease to be determined and the most appropriate dose of medication to be given.

Suitably, the detecting means comprises a sensing means, for example a biosensor that is able to specifically detect one or more given biochemical markers. In general terms, 'biosensor' means a sensor, which responds to the presence of particular biochemical markers and converts it into a correlated measurable signal.

Biosensors may generally be classified by four different principles: bioaffinity, biocatalytic, transmembrane and cell sensors. In a bioaffinity sensor, the biochemical marker is recognised by immobilised recognition units on the sensing layer. In a biocatalytic sensor, the biochemical marker is converted by, for example immobilised enzymes on the sensing layer, to products. In a transmembrane sensor, either transport or channel proteins, or receptor proteins are incorporated into a membrane in the sensing layer. These structures either move the biochemical marker through the membrane, bind the biochemical marker and open a channel for another species or subsequently activate a separate enzymatic cascade. A cell sensor utilises immobilised living cells in the sensing layer to either convert or bind the biochemical marker. The various different types of sensors are described in more detail by Ziegler and G pel in Current Opinion in Chemical Biology 1998, 2: 585-591 which is incorporated herein in its entirety by reference.

Suitably, the biosensor comprises at least two main parts: a sensing layer and a transducer layer.

The sensing layer of the biosensor suitably captures the target biochemical markers either by physical binding or by characteristic interactions in a highly selective manner. The sensing layer may comprise one or more of the following types of material: enzymes, receptors, micro-organisms, antibodies, antigens, nucleic acids, cells, peptides, proteins, biochemicals. Alternatively, artificial or synthetic materials analogous to those listed above may be used in the sensing layer. Such artificial or synthetic materials may be known as 'artificial receptors', 'artificial antibodies', 'synthetic DNA', 'synthetic peptides' etc., for example a material known as the 'Molecularly Imprinted Polymer (MIP)'.

In one aspect, the sensing layer comprises a renewable sensing surface, i.e. the sensing surface is regenerated so that it can be used to detect the biochemical markers more than once.

Immobilisation of the recognition units on the sensing surface is achieved by either forming a chemical bond with the surface, or by encapsulating the recognition units in a layer of porous material coated onto the surface, such as Sol Gel, Hydro Gel, and polymer membranes. If transmembrane proteins are used as recognition units, they may also be embedded into a lipid membrane (or cell membrane) anchored onto the sensing surface by chemical bonds.

The sensing surface described above can be developed as a self-generating surface which can be used continuously for generation of sensing signals in response to the presence of targeting analytes. Such surfaces include, typically, biocatalyst as recognition molecules. A biocatalyst does not change its chemical and physical structures but helps to speed up specific reaction of the analytes Another type of renewable sensing surface requires incorporation of a surface renewing process between two sequential measurements, to remove bound analytes from the recognition molecules. This is achieved typically by changing the chemical environment of the sensing surface, e.g. the biochemical marker(s) can be removed from the sensing surface by lowering the pH of the sensor.

In another aspect, the biosensor comprises a removable non-renewable sensing surface. In such a scheme, the sensing surface is positioned on a removable component, which can be removed and replaced by a new one in between one measurement and the next.

The transducer layer of the biosensor acts such as to translate the molecular interactions, used to sense the target, into a measurable signal. There are a range of mechanisms that may be used to realise this conversion, for example optical, electrical, semi-conductor, thermal and acoustic. The most commonly used methods are electrochemical and optical transducers. The former convert biological interactions into proportional electrical signals, and the latter into light signals. Other physical signals used include heat, sound, mass and magnetism.

In a further aspect, the sensing means comprises one or more non-specific bio- or chemosensors, e.g. an 'electronic nose' (or 'electronic tongue'). Certain diseases are associated with unique body odour signatures, which may be useful in assessing the extent and severity of the disease at a given time. The electronic nose uses arrays of sensing elements, typically thin film coating of, for example, polymers (e.g. conducting polymer—polypyrrole) or metal oxides, such as tin oxide and zinc oxide. Each sensing element is chosen to have different absorption characteristics for the biomarker(s) being investigated such that a matrix array of elements can be used to deconvolute components in a test sample. Signals generated include variations in electrical conductivity, weight/mass or acoustic attenuation. Deconvolution of such overlapped responses from the sensing element array is achieved by application of an appropriate mathematical algorithm (e.g. artificial neural-network or chemometrics) to generate molecular ID(s) of biomarker(s). Therefore, the electronic nose can be used to determine mixtures of odours simultaneously or individually. The sensing elements in an electronic nose have little specific selectivity. The specificity of an electronic nose is achieved by deconvolution of an array of responses resulting from various sensing elements. Therefore, the technology can detect a range of molecules, determined by the materials of sensing elements.

The absorption of gas molecules by the sensing elements of an electronic nose is a reversible process, and therefore an electronic nose can be repeatedly used over the lifetime of the sensing material.

In certain situations, a pre-separation process can be placed in front of a non-specific sensor to separate various species within the analytical sample, which are detected sequentially by a non-selective sensor. Separation technologies suitable for such applications can be a miniaturised gas chromatograph device, a capillary electrophoresis chip ('lab on a chip'), or other electrophoresis device, (such as gel electrophoresis and free flow electrophoresis, dielectrophoretic separation etc.), or simply, a piece of lateral flow membrane.

A number of biosensors, which are currently available, may be adapted for use in the medicament dispensing system of the present invention. Such biosensors include, but are not limited to: ZeptoCHIPs and ZeptoTAS (available from Zeptosens AG), BeadArray™ (available from Illumina), ProcessMonitor, MultiTRACE, Dialysis Probe etc (available from TRACE Biotech AG), SIRE Biosensors (available from Chemel AB), LIBRA α, LibraNose etc (available from Technobiochip), VOCcheck, VOCmeter etc (available from Applied Sensors), Cyranose 320 (available from Cyrano Sciences), Osmetech Microbial Analyser™, SENSA (available from Osmetech), Implanted Glucose Biosensor (available from BYBD), BreathAlert™, Breath Checker (available from Comfort House), SAFE™ Personal Alcohol Breath Analyzer available from Craig Medical), ZNOSE™ (available from Electronic Sensor Technology), PROMETHEUS, FOX, Astree, etc (available from Alpha M.O.S.), GlucoWatch® (available from Cygnus) and The Glucose Sensor (available from Animas Corp).

In another aspect, the detecting means directly detects the presence of the biomarker(s) of interest.

Suitably, the detecting means comprises spectroscopic detecting means for direct spectroscopic detection of one or more biochemical marker(s). In variations, the spectroscopic detecting means are used in combination with one or more biosensors incorporating a sensing layer and transducer layer or as an alternative thereto.

The spectroscopic detecting means may be employed in either destructive or non-destructive methods of detection of the relevant biomarker(s) and utilise any suitable analytical methods and techniques.

Suitable non-destructive detection methods include those using spectroscopic detecting means to detect any suitable spectral characteristics of the biomarker(s). Examples of suitable characteristics include the absorbance, reflectance, scattering, fluorescence, magnetic resonance and luminescence characteristics of the biomarker(s). It will be appreciated that the particular spectroscopic technique employed will be chosen in view of the properties of the particular biomarker of interest. Particularly suitable methods include infra red and Raman spectroscopy.

Suitable destructive detection methods include those using various techniques to break up the relevant biomarker(s) into component parts thereof. The fragments are then analyzed e.g. for characteristic fragmentation fingerprints. Suitable methods include gas chromatography, mass spectrometry and ion mobility spectroscopy. It will be appreciated that the particular method employed will be chosen in view of the biomarker of interest and its fragmentation characteristics.

In aspects herein, plural detection methods are employed to characterize any particular biomarker(s). In one particular aspect, plural (e.g. spectroscopic) detecting means are arranged in array fashion.

The medicament dispensing system comprises electronic processing means for processing information obtainable from the detecting means.

Suitably, the electronic processing means comprises a micro-controller with associated analogue and digital electronics, and interfaces. The electronic processing means receives the output electronic signal from the detecting means, amplifying it and converting it into appropriate analogue or digital signal format at an electronic interface. By analyzing the signal using an appropriate analogue computer (circuitry), or using appropriate algorithms (software) in the case of a digital computer, a biomarker specific response can be determined, and correlated with the extent and severity of the disease at that time. The quantity of medicament required to treat the disease can then be determined based on the efficacy of the drug and optimum response of the dosing curve at the severity level of the disease as measured. The correlation between the disease status and the control parameters for drug dosing are pre-determined from clinical studies and pre-stored in the device, in the form of a series of electronic circuit settings (analogue system), or data stored in the memory in the case where a digital system is being used.

If the output signal from the detection means is not an electrical signal, for example the signal is light (fluorescence spectra, absorption, luminescence etc), heat, acoustic, etc., an appropriate detector based on a corresponding principle (photo-electric, thermoelectric, or acousto-electric, etc.) is used to convert the signal into an electrical signal before it is connected to the above described electronics amplification, signal conditioning and processing electronics for further analysis.

The micro-controller is typically a Single-Chip-Computer, which is a miniature computer fabricated on a single semiconductor chip, containing central processing unit (CPU), on board memories (e.g. RAM and EPROM), and appropriate interfaces (e.g. timer/counter, parallel digital interfaces, A/D, D/A interface). The single-chip-computer can be programmed through a system development kit. Using such a kit, appropriate components, such as a working-clock oscillator, resistors, and capacitors etc, can be tested and wired with the computer to allow the desired functions and the software programme tested before it is 'permanently' fixed onto the memory within the computer for system control and performing mathematical analysis. The computer will directly convert the analogue signal from the detection means into digital signals and perform mathematical analysis to extract all necessary information from the signal, comparing the measured result with the results stored in the computer database (e.g. stored within a suitable Look up table), decide and control subsequent actuation via sending out appropriate control electrical signal to the actuator. The system will also be able to display the result via associated LED or LCD, or other display devices and communicate with other database systems via a series/parallel interface for record and for telemedicine purpose.

Alternately, a micro-controller can be developed based on a single-board-computer, which integrates a central processing unit (CPU), memories (e.g. RAM, EPROM), and interfaces (A/D, D/A, Counter/Timers, etc.) on to a single printed circuit board. It functions in much the same manner as the single-chip-computer.

Alternatively, an analogue computer is used in place of a digital single-chip or single-board computer and the signal is processed in an all-analogue form. Corresponding control signals for driving actuation mechanisms and result display are also all analogue signals. Communication with other systems is achieved via appropriate interfaces.

Suitably, there is provided an electronic data management system that is either integral with or communicates with the electronic processing means. The electronic data management system typically has input/output capability and comprises a memory for storage of data; a microprocessor for performing operations on said data; and a transmitter for transmitting a signal relating to the data or the outcome of an operation on the data.

Suitably, the medicament dispensing system additionally comprises a data input system for user input of data to the electronic data management system. Preferably, the data input system comprises a man machine interface (MMI) preferably selected from a keypad, voice recognition interface, graphical user interface (GUI) or biometrics interface.

Suitably, the electronic data management system is adapted to receive and process data relating to initial settings of any feature; medicament-related prescribing data; and data relating to the patient. The data is, for example, input to the data management system by the doctor, nurse, pharmacist or even the patient or it may be factory pre-set. Examples of patient-related data for inputting could for example, include the age, sex, bodyweight and the general medical/prescription history of the patient. Examples of medicament-related data could include the 'standard' dosage regime and permissible variations within that regime.

Energy may be conserved by a variety of means to enable the system to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic components, such as visual display units or sensors, in order to power these devices only when they are required to perform a particular sequence of events. Thus different electronic components may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual components in order to minimize current in the event of failure.

In some control applications, components that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic processing means and/or electronic data management system to the user. The display may for example, comprise a screen such as an LED or LCD screen. More preferably the visual display unit is associable with the body of the medicament dispenser.

Suitably, the medicament dispensing system additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped for accommodation within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infrared link or any other suitable wireless communications link.

In one aspect, the medicament dispensing system includes an electronic dose reminder system. This may be configured to have any suitable form and may be powered by mains, stored (e.g. battery) or self-regenerating (e.g. solar) energy power source.

The electronic dose reminder system comprises an electronic timer for timing an elapsed time period corresponding to the time since the last actuation of the device; a dose interval memory for storing data relating to a prescribed dose interval time period; and a patient alerter for alerting a user. The alerter activates when the elapsed time period exceeds the prescribed dose interval time period.

The electronic timer progressively times the period since the last actuation of the medicament dispensing means (the 'elapsed time period'). The timer can have any suitable electronic form. The significance of the 'elapsed time period' is that in use, it typically corresponds to the time elapsed since the previous dose delivery event.

The timer may be configured to include an automatic re-zeroing feature such that on subsequent actuation of the device the timer count starts again from zero.

The dose interval memory stores data relating to a prescribed dose interval time period. By way of examples, if the medicament is to be taken twice a day at a regular interval, the prescribed dose interval may be set as twelve hours, or for a once daily treatment the value may be set at twenty four hours. In aspects, the system may be configured to allow for ready readjustment of the prescribed dose interval time period, or it may be configured in secure fashion such that any readjustment may be made only by a designated prescriber (e.g. a medical professional or pharmacist). Password and/or other security means may be employed. The prescribed dose interval may be configured to be variable over a particular course of treatment, or alternatively it may be fixed at a set dose interval over the full course of treatment.

The patient alerter is designed to communicate an alert to the user. The alerter activates only when the holding time period exceeds the prescribed dose interval time period. By way of an example, for a once daily treatment with a prescribed dose interval of twenty four hours, the alerter would activate only when the holding time period, as timed by the electronic timer, exceeds twenty four hours since at this point another dose is due to be taken. It may thus, be appreciated that the alerter acts functionally as a reminder to the patient that a dose is due to be taken.

The alerter may in aspects, comprise a visual device, such as a liquid crystal display (LCD) or an array of light-emitting diodes (LEDs), connected to a battery-driven timing device of any convenient kind known to those skilled in the art. The visual device may be configured to display information such as the actual time or the elapsed time from the taking of a previous dosage and may have superimposed thereon additional messages, such as a textual instruction to take a dose of the medicament. Alternatively, the instruction to take the medicament may be conveyed merely by displaying a warning color or by causing the display to flash or in any other way.

In a further alternative arrangement, no specific time or elapsed time information is displayed, but the alerter merely provides a warning signal that indicates the necessary action to the user.

Depending upon the lifestyle of the user, additional or alternative warnings may be of greater assistance than purely visual warnings. Accordingly, it is envisaged that the alerter may provide audible and/or tactile warnings, such as vibration, instead of (or in addition to) visual warnings.

The alerter may provide a single, one-off alert. More preferably, the alerter is configured to provide the alert over a set period of time (the 'alerting time period' or 'alerting window'). In one aspect, the alerting time period is calculated as a function of (e.g. fraction of) the dose interval time period. For example, for a twice-daily treatment with a dose interval time period of twelve hours, the alerting time period may be set as half that period (i.e. six hours). In this case, the alert is then provided for the six hours immediately following the activation of the alert.

The reminder system is typically configured such that the alerting signal cuts off when the user removes the medicament delivery device from the holder to enable dosing of medicament therefrom. The system is then reset. Other manual cutoffs/overrides may also be included.

Suitably, the medicament dispensing system herein additionally comprises an actuation detector for detecting actuation of the medicament dispensing means, wherein said actuation detector transmits actuation data to the electronic data management system.

The medicament dispensing means may additionally comprise a safety mechanism to prevent unintended multiple actuations. The patient is thereby, for example, protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispensing system additionally comprises a release detector for detecting release of medicament from the medicament dispensing means, wherein said release detector transmits release data to the electronic data management system.

Suitably, the medicament dispensing means additionally comprises a shake detector for detecting shaking of the medicament container (e.g. prior to dispensing), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the memory on the electronic data management system includes a dose memory (e.g. look up table form) for storing dosage data and reference is made to the dose memory in calculating the optimum amount of medicament to dispense.

A suitable power source such as a battery, clockwork energy store, solar cell, fuel cell or kinetics-driven cell will be provided as required to any electronic component herein. The power source may be arranged to be rechargeable or reloadable.

Suitably, the medicament dispensing system additionally comprises one or more sensors for sensing environmental conditions, particularly those conditions which may affect the patient's therapeutic needs. Thus, ambient temperature, humidity, air pollution, ozone and other similar factors may be sensed. The readings may simply be arranged for display to the patient or in aspects, may be factored into the dosage calculation, perhaps after receipt of a specific confirmation by the patient that such factoring in is to be applied.

Suitably, the medicament dispensing system additionally comprises a communicator for wireless communication with a network computer system to enable transfer of data between the network computer system and the electronic data management system. Dispensers employing such communicators are described in pending PCT Applications Nos. PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source is made available thereto. More preferably, information from the user-specific network address can be made available to the remote information source.

In one aspect, the remote information source is a medicament prescriber, for example a doctor's practice. Information transferred from the medicament prescriber may thus, comprise changes to prescription details, automatic prescription updates or training information. Information transferred to the medicament prescriber may comprise compliance information, that is to say information relating to the patient's compliance with a set-prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

Suitably, the medicament dispensing system further comprises a sampling means. The sampling means is adapted to sample the patient's breath, skin, sweat, urine, blood or other bodily fluid. Suitably, the sampling means directs the patient's sample into the detecting means. The sampling means may comprise for example a mouthpiece into which the patient exhales or any other sampling means suitable for sampling the particular fluid or bodily excretion.

The medicament dispensing system comprises medicament dispensing means for dispensing a quantity (e.g. volume or mass) of medicament determinable by the electronic processing means. The quantity may in aspects, correspond to a full dose or it may correspond to a part dose.

Suitably, the medicament dispensing means comprises one or more medicament container(s) for storing the medicament and one or more dispensing mechanism(s) for dispensing a quantity of medicament determinable by the electronic processing means. The dispensing quantity (e.g. dose or part-dose) is in one aspect adjusted to an appropriate setting by moving an adjustable actuator into appropriate position corresponding to the dosage required for the determined disease state or severity.

The quantity of medicament to be dispensed (i.e. dose setting) is in one aspect, automatically controlled by the micro-controller electronically via an appropriate interface and electromechanical systems (or micro electromechanical system—MEMS).

In another aspect, the quantity of medicament to be dispensed is set manually by the patient responsive to dose guidance determined by the electronic processing means and indicated to the patient (e.g. visually, on an electronic display).

In one aspect, the quantity of medicament for dispensing is metered from a reservoir of medicament (e.g. in powder or fluid form) by use of any suitable metering means.

Suitably, the meter comprises a valve (for example, a linear or rotary valve) and/or a piston and/or a load cell. In another aspect, the meter comprises a plunger, such as might exist in a syringe.

Suitably, the meter comprises at least one metering chamber. In one embodiment, on actuation of the meter, the or each metering chamber moves into fluid communication with the reservoir.

In one embodiment, the meter and the reservoir are relatively rotatable with respect to each other about a common central axis. Preferably, the or each metering chamber is adapted to be in fluid communication selectively with the reservoir or with the patient.

The or each metering chamber may have a variable volume. Alternatively, the or each metering chamber may have a fixed volume which is variable by insertion of a plunger or piston. The or each metering chamber may be formed from expandable material and/or have a telescopic or concertina arrangement.

In aspects, the medicament dispensing means is selected from the group consisting of a reservoir dry powder inhaler (RDPI), a multi-dose dry powder inhaler (MDPI), a metered dose inhaler (MDI) and a liquid spray inhaler (LSI).

By reservoir dry powder inhaler (RDPI) it is meant an inhaler having a reservoir form container pack suitable for containing multiple (un-metered doses) of medicament product in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose container pack containing (or otherwise carrying) multiple, define doses (or parts thereof) of medicament product. In a preferred aspect, the carrier has a blister pack form, but it could also, for example, comprise a capsule-based pack form or a carrier onto which medicament has been applied by any suitable process including printing, painting and vacuum occlusion.

In one aspect, the multi-dose pack is a blister pack comprising multiple blisters for containment of medicament product in dry powder form. The blisters are typically arranged in regular fashion for ease of release of medicament therefrom.

In one aspect, the multi-dose blister pack comprises plural blisters arranged in generally circular fashion on a disc-form blister pack. In another aspect, the multi-dose blister pack is elongate in form, for example comprising a strip or a tape.

Preferably, the multi-dose blister pack is defined between two members peelably secured to one another. U.S. Pat. No. 5,860,419 in the name of Glaxo Group Ltd describes medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 µl, such as 25 µl, 50 µl or 63 µl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration arid the chamber has an internal configuration such that a metered volume is defined therebetween and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085.

By liquid spray inhaler (LSI) it is meant a medicament dispenser suitable for dispensing medicament in spray form, wherein the medicament is typically formulated in liquid or solution form and comprised in a liquid container. The container is typically provided with a means of metering to a spray generator, which imparts energy to the liquid or solution, thereby generating a spray for inhalation by the patient. The spray generator, in aspects, comprises a vibrating element (e.g. a mesh) that provides vibrational energy to the formulation, thereby resulting in its aerosolisation. In other aspects, the spray generator comprises a pump mechanism, which either delivers the medicament directly to the patient (as a liquid spray) or which delivers the medicament to an intermediate position at which further energy is supplied thereto to further propel, aerosolize or otherwise direct the medicament dose to the patient.

The dispensing mechanism controls the amount of drug released. This dosage control may be achieved via various control means. In one aspect, a valve, for example a metering valve is employed. Alternatively, drug-releasing membrane, drug containing capillaries, or other releasable captures can be used to adjust the amount of drug release in the case of dry powders. Alternatively, regulation of the diameter of the medicament exit port may be used to regulate the quantity of medicament dispensed.

The dispensing mechanism suitable for the device includes, but is not limited to the use of air jet (e.g. $CO_2$), vapor jet and acoustic atomization processes. Alternatively, mechanical vibration based on atomization can be used to dispense aerosols. Other possible dispensing means may involve using ablation processes to generate aerosols, e.g. using ultrasonic pulsing or even a laser.

In particular aspects herein, the medicament dispensing system is provided with plural medicament dispensing means, each for use in the delivery of a component part of a combination medicament product. The quantity of medicament dispensed by each medicament dispensing means is determinable by the electronic processing means, which thereby enables the delivery of 'tailored' combination products wherein the relative amounts of each medicament component part thereof is variable in response to the patient's detected therapeutic need.

Suitably, the medicament dispensing system comprises first medicament dispensing means and at least one further medicament dispensing means.

Suitably, the medicament dispensing system comprises
(a) a first medicament container for containing a first medicament component and first release means for releasing the contents of said first medicament container; and
(b) at least one further medicament container for containing at least one further medicament component and at least one further release means for releasing the contents of each said at least one further medicament container, wherein the first medicament component is kept separate from the at least one further medicament component until the point of release thereof for delivery in combination.

Suitably, in combination, the first medicament and at least one further medicament comprise a combination product. That is to say, that when combined together the distinct active medicament doses released by actuation of the device form a dose of a 'multi-active' medicament treatment.

On actuation, the combination medicament dispensing is designed to deliver a dose portion of the first medicament and a dose portion of each at least one further medicament. The term 'dose portion' is employed because the distinct 'portions' are brought together on delivery to form a combination (i.e. multi-active) product dose. In accord with the present invention, the ratio of incorporation of each active component of the combination is variable in response to input from the electronic processing means.

In one particular aspect, the first medicament container contains plural co-formulation compatible medicament components, and each at least one further medicament container contains at least one co-formulation incompatible medicament component.

The term 'co-formulation compatible' herein is used to mean compatible in the sense of being amenable to co-formulation, perhaps even displaying synergetic co-formulation characteristics. The term 'co-formulation incompatible' is used to mean the reverse, that is to say for whatever reason including chemical or physical incompatibility or simply lack of synergetic characteristics or benefits, the medicament components are either non-amenable to co-formulation or for whatever reason, including for development simplicity, preferably not co-formulated.

In a preferred embodiment, the system herein is designed to treat a disease by inhalation of medicament, either inhalation through the mouth or the nose. However, a system is also envisaged and is within the scope of the invention, where the medicament is administered by an alternative method, for example by injection.

In use, the patient exhales (in the case of an inhalation system) into the detecting means, one or more biochemical markers being present in the exhaled breath. These biochemical markers are detected by the detecting means which produces an output signal correlating with the concentration of biochemical markers. It is possible that the detecting means is such that it is able to detect more than one biochemical marker. The output signal from the detecting means is processed by the electronic processing means and will determine the severity of the disease at that particular moment and the required dosage of drug or drug combination. The electronic processing unit will programme the dispensing means such that when the patient takes his medication he will automatically receive an appropriate quantity of medicament.

The invention will now be described in more detail with reference to the following drawings:

DETAILED DESCRIPTION OF THE DRAWINGS

Figure 1A:
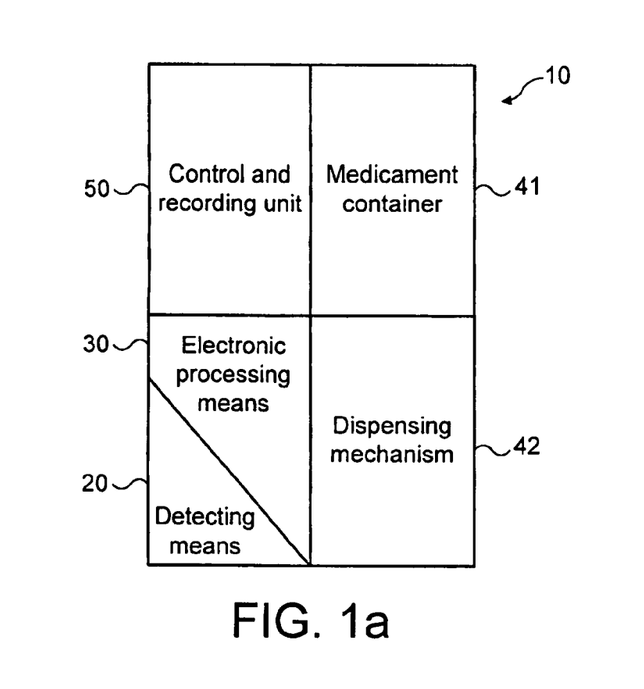
FIGS. 1A, 1B and 1C show schematic representations of the system where the detecting means is integrated with the whole device, the detecting means is as an attachment to the device, and the detecting means is remote to the device.
Figure 1B:
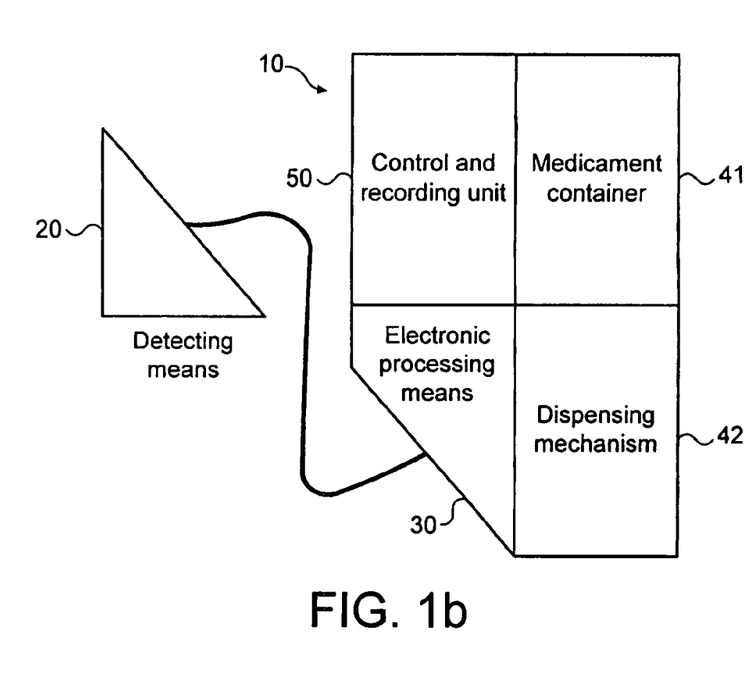
Figure 1C:
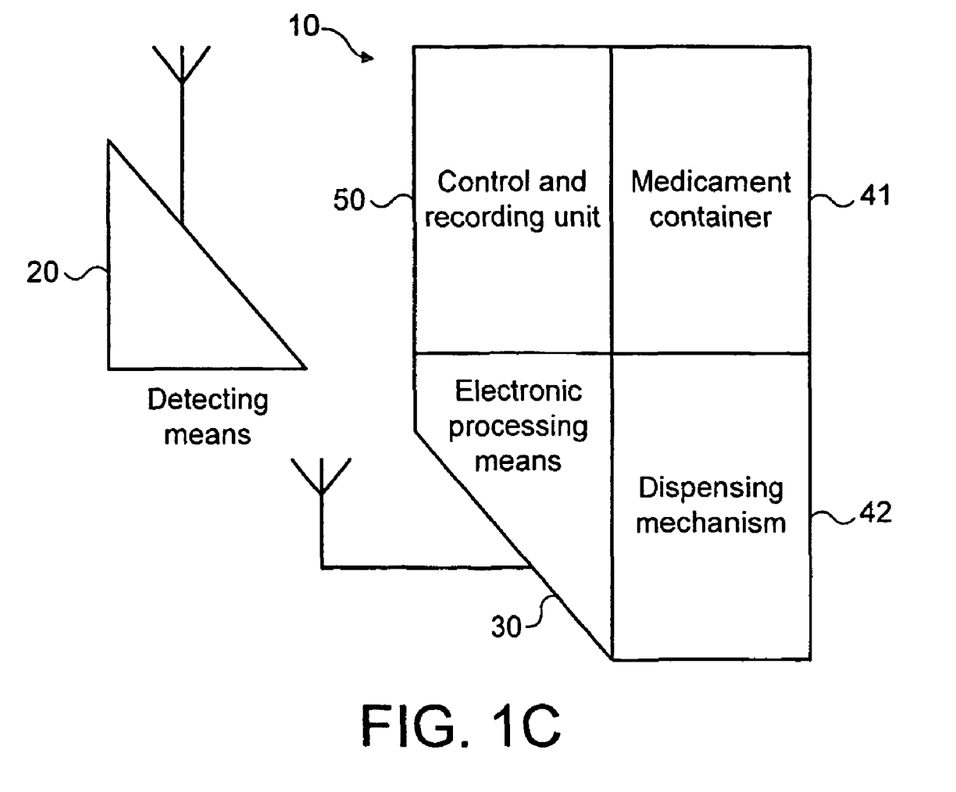

FIGS. 1A, 1B and 1C all show a schematic representation of the medicament dispensing system of the invention. The medicament dispensing system 10 comprises detecting means 20, electronic processing means 30 and medicament dispensing means comprising medicament container 41 and dispensing mechanism 42. The detecting means comprises a sampling means (not shown) for example a mouthpiece into which a patient exhales. Specified biochemical markers in the exhaled breath are detected by the detecting means 20 and the data processed by the electronic processing means 30. The electronic processing means 30 determines the required quantity of medication using the control and recording unit 50. Dispensing mechanism 42 dispenses the medication from medicament container 41 to the patient. In some cases, medicament container 41 and/or dispensing mechanism 42 may be physically integrated with part of the detection means 20, e.g. a shared mouthpiece.

Figure 2:
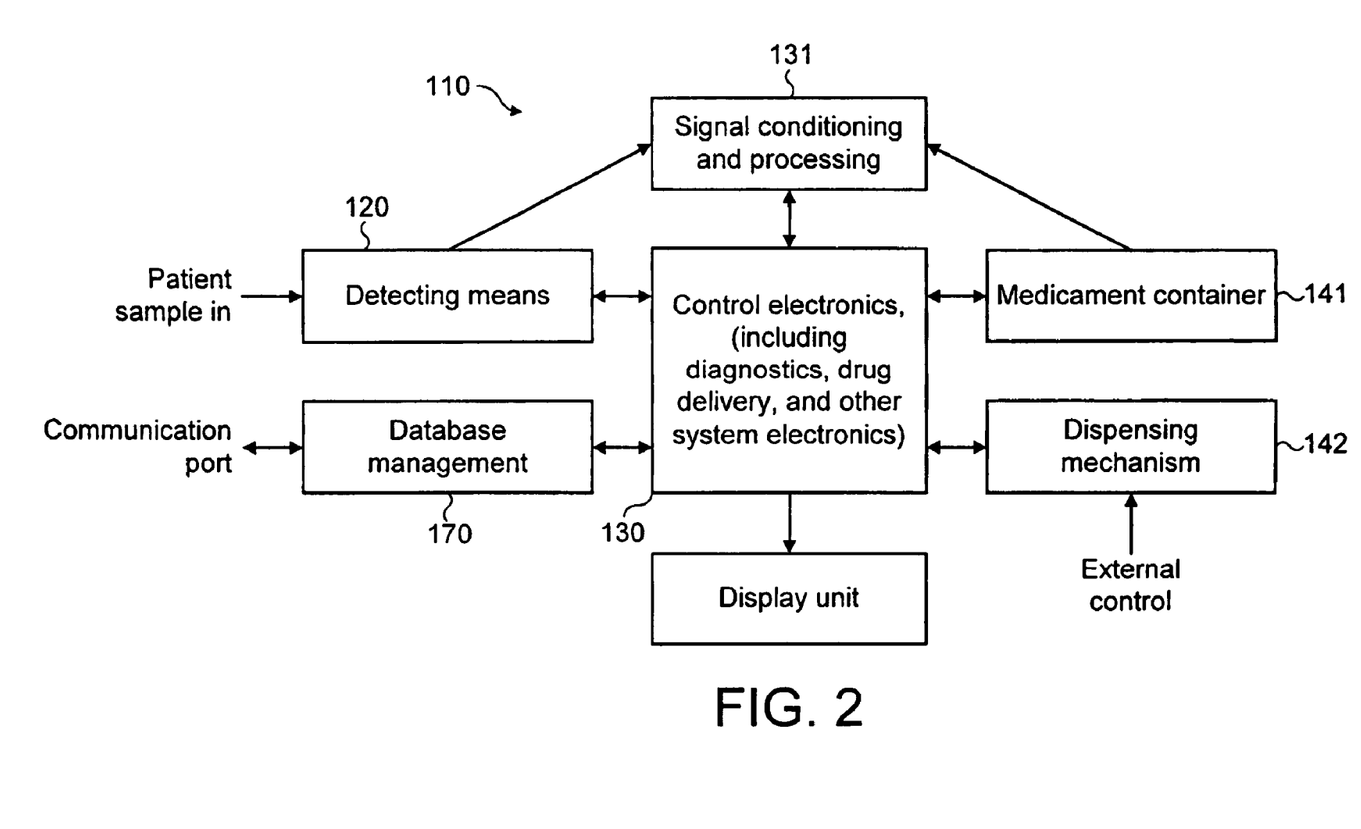
FIG. 2 shows a schematic diagram of the various components of the medicament dispensing system.

FIG. 2 shows a schematic functioning diagram of the system 110. The detecting means 120 may contain one or more sensing/transducing elements of any suitable principles, including those for diagnostics sensing and those for feedback for device control and referencing purposes. In the case of an inhalation device, the detecting means is usually housed in a mouthpiece. The signal conditioning and processing unit 131 includes signal pre-amplification and other necessary signal modification circuits before its converting to digital signal by control electronics unit 130 (via A/D interface). This is a key unit consisting of micro-controller and affiliated electronics. The control electronic unit 130 receives measurement signals, system control feedback, such as temperature, drug remaining in reservoir, actuator statues, and others system parameters sending back by various sensors in the system. All the information is processed according the controlling software (or analogue circuitry) developed for the system which tells the unit 130 to take appropriate actions in responding to particular input signals. It also controls system display unit 160 to display proper message for user, and communicates with other systems via telecommunication interface. It will interact with database management software 170 to allow measurement data to be organized appropriately and to extract information required to determine disease severity or dose required to deliver etc. The medicament container 141 is basically a drug storage facility with necessary sensors and actuators controllable by the micro-controller. Drug dispensing mechanism 142 is a (micro) mechanical or electromechanical actuation system, which will respond to the microcontroller's signal to adjust drug-dispensing volume and activate subsequent delivery actions.

The medicament dispensing system of the invention is suitable for dispensing medicament combinations, particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Preferred respiratory medicaments are selected from albuterol, salmeterol, fluticasone propionate and beclomethasone dipropionate and salts or solvates thereof, e.g., the sulphate of albuterol and the xinafoate of salmeterol.

Preferred medicament combination products contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination of components comprises fluticasone propionate and salmeterol, or a salt thereof (particularly the xinafoate salt). A further combination of components of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

Aerosol formulations suitable for use with metered dose inhaler (MDI) dispensers typically comprise a propellant. Suitable propellants include P11, P114 and P12, and the CFC-free hydrofluoroalkane propellants HFA-134a and HFA-227.

The MDI aerosol formulation may additionally contain a volatile adjuvant such as a saturated hydrocarbon for example propane, n-butane, isobutane, pentane and isopentane or a dialkyl ether for example dimethyl ether. In general, up to 50% w/w of the propellant may comprise a volatile hydrocarbon, for example 1 to 30% w/w. However, formulations, which are free or substantially free of volatile adjuvants are preferred. In certain cases, it may be desirable to include appropriate amounts of water, which can be advantageous in modifying the dielectric properties of the propellant.

A polar co-solvent such as $C_{2-6}$ aliphatic alcohols and polyols e.g. ethanol, isopropanol and propylene glycol, preferably ethanol, may be included in the MDI aerosol formulation in the desired amount to improve the dispersion of the formulation, either as the only excipient or in addition to other excipients such as surfactants. Suitably, the drug formulation may contain 0.01 to 30% w/w based on the propellant of a polar co-solvent e.g. ethanol, preferably 0.1 to 20% w/w e.g. about 0.1 to 15% w/w. In aspects herein, the solvent is added in sufficient quantities to solubilise the part or all of the medicament component, such formulations being commonly referred to as solution formulations.

A surfactant may also be employed in the MDI aerosol formulation. Examples of conventional surfactants are disclosed in EP-A-372,777. The amount of surfactant employed is desirable in the range 0.0001% to 50% weight to weight ratio relative to the medicament, in particular, 0.05 to 5% weight to weight ratio.

The final aerosol formulation desirably contains 0.005-10% w/w, preferably 0.005 to 5% w/w, especially 0.01 to 1.0% w/w, of medicament relative to the total weight of the formulation.

The medicament dispensing system of the invention is in one aspect suitable for dispensing medicament for the treatment of respiratory disorders such as disorders of the lungs and bronchial tracts including asthma and chronic obstructive pulmonary disorder (COPD). In another aspect, the invention is suitable for dispensing medicament for the treatment of a condition requiring treatment by the systemic circulation of medicament, for example migraine, diabetes, pain relief e.g. inhaled morphine.

Accordingly, there is provided the use of a medicament dispensing system according to the invention for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a medicament dispensing system of the present invention.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A hand-held inhalation device for treatment of a disease by inhalation of medicament through the mouth or nose of a patient comprising:
   (i) a medicament dispenser for dispensing a quantity of medicament,
   (ii) a detector for detecting one or more biochemical marker(s) in an exhaled breath of the patient indicative of said disease, the detector comprising a sampler into which the patient is able to exhale, and;
   (iii) an electronic processor for processing information obtainable from the detector;
   wherein said medicament dispenser dispenses a quantity of medicament determinable by the electronic processor, and; said medicament dispenser, detector and electronic processor are integrated components of the handheld inhalation device.

2. An inhalation device according to claim 1, wherein the detector comprises a sensor.

3. An inhalation device according to claim 2, wherein the sensor is a non-specific bio- or chemosensor.

4. An inhalation device according to claim 3, wherein the detector further comprises a pre-separation device.

5. An inhalation device according to claim 4, wherein the pre-separation device comprises a miniaturised gas chromatograph device, a capillary electrophoresis chip or other electrophoresis device, or a lateral flow membrane.

6. An inhalation device according to claim 2, wherein the sensor comprises a biosensor.

7. An inhalation device according to claim 6, wherein said biosensor comprises a sensing layer and a transducer layer.

8. An inhalation device according to claim 7, wherein said sensing layer comprises one or more materials selected from the group consisting of enzymes, receptors, micro-organisms, antibodies, antigens, nucleic acids, cells, peptides, proteins and biochemicals.

9. An inhalation device according to claim 7 wherein the sensing layer comprises one or more artificial or synthetic materials analogous to enzymes, receptors, micro-organism, antibodies, antigens, nucleic acids, cells, peptides, proteins and biochemicals.

10. An inhalation device according to claim 7, wherein the sensing layer comprises a renewable sensing surface.

11. An inhalation device according to claim 7, wherein the sensing layer comprises a non-renewable sensing surface.

12. An inhalation device according to claim 11, wherein the sensing layer comprises a disposable component incorporating the non-renewable sensing surface.

13. An inhalation device according to claim 9, wherein said transducer layer comprises an optical, electrical, semi-conductor, thermal or acoustic mechanism.

14. An inhalation device according to claim 1, wherein the detector comprises spectroscopic detecting means for direct spectroscopic detection of one or more biochemical marker (s).

15. An inhalation device according to claim 14, wherein the spectroscopic detector is suitable for use in infra red and Raman spectroscopic detection methods.

16. An inhalation device according to claim 1, wherein said device comprises more than one detector for detecting one or more biochemical marker(s).

17. An inhalation device according to claim 16, wherein said said detectors are arranged in array fashion.

18. An inhalation device according to claim 1, wherein the electronic processor comprises a micro-controller with associated analogue and digital electronics and interfaces.

19. An inhalation device according to claim 18, wherein the electronic processor further comprises an amplifier for amplifying the signal received from the detector.

20. An inhalation device according to claim 1, additionally comprising an electronic data management system in communication with the electronic processor.

21. An inhalation device according to claim 20, wherein the electronic data management system includes a database and the electronic processor makes reference to that database in determining the quantity of medicament to dispense from the dispenser.

22. An inhalation device according to claim 1, wherein the medicament dispenser comprises a medicament container and a dispensing mechanism.

23. An inhalation device according to claim 22, wherein the dispensing mechanism is automatically set in direct response to the determination of the electronic processor.

24. An inhalation device according to claim 22, wherein the dispensing mechanism is set manually in response to the determination of the electronic processor.

25. An inhalation device according to claim 1, wherein the medicament dispenser is selected from the group consisting of a reservoir dry powder inhaler, a multi-dose dry powder inhaler, a metered dose inhaler and a liquid spray inhaler.

26. An inhalation device according to claim 1, wherein said device comprises a plurality of medicament dispensers, each providing a component part of a combination medicament product.

27. An inhalation device according to claim 26, wherein the dispensing ratio of each component part of the combination medicament product is variable in response to input from the electronic processor.

28. An inhalation device according to claim 26 comprising:
 (a) a first medicament container for containing a first medicament component and first releaser for releasing the contents of said first medicament container; and
 (b) at least one further medicament container for containing at least one further medicament component and at least one further releaser for releasing the contents of each said at least one further medicament container,
 wherein the first medicament component is kept separate from the at least one further medicament component until the point of release thereof for delivery in combination.

\* \* \* \* \*